United States Patent [19]

Parsons et al.

[11] Patent Number: 5,248,479
[45] Date of Patent: Sep. 28, 1993

[54] AGGLUTINATION REACTION DEVICE HAVING GEOMETRICALLY MODIFIED CHAMBERS

[75] Inventors: Robert G. Parsons, Green Oaks; Bob O. Basore, Evanston; Michael B. O'Connell, Waukegan; Kevin J. Forney, Chicago, all of Ill.; Paul J. Ropella, Racine, Wis.; Andrew J. Muetterties, Mundelein, Ill.

[73] Assignee: Abbott Laboratories, Abbott Park, Ill.

[21] Appl. No.: 995,303

[22] Filed: Dec. 22, 1992

Related U.S. Application Data

[63] Continuation of Ser. No. 614,817, Nov. 16, 1990, abandoned, which is a continuation-in-part of Ser. No. 138,256, Dec. 23, 1987, abandoned.

[51] Int. Cl.⁵ .............................. G01N 21/00
[52] U.S. Cl. ........................ 422/58; 422/56; 422/100; 436/69
[58] Field of Search .................. 422/55-58, 422/100-101; 436/63, 69, 165, 169-170, 177, 180; 424/2, 11

[56] References Cited

U.S. PATENT DOCUMENTS 4,906,439  3/1990  Grenner ........................... 422/58

Primary Examiner—Lyle A. Alexander
Attorney, Agent, or Firm—Gregory W. Steele; Lawrence S. Pope

[57] ABSTRACT

A device for performing agglutination immunoassay reactions and the like is disclosed. The device includes a first hydrophilic layer, a second liquid-occlusive layer parallel to and overlying the first layer, and a third layer parallel to and overlying the second layer. The third layer has a transparent opening for observing particles. The second layer is interposed between and in adherent relationship to the first and third layers. The second layer has at least one slot defining a channel for directing liquid conducted by capillary action through the chamber defined in conjunction with the first and third layers. This chamber has a proximate zone and a distal zone. The geometry of the chamber is modified to provide preferably outwardly diverging walls and provide a flowpath having different rates of flow per unit area along the paths. This arrangement of different paths in the chamber allows agglutination reactions in the chamber to result in the formation of a non-random pattern of aggregated particles in the distal zone of the chamber. Such a non-random pattern is more readily observable than a random pattern of aggregated particles.

19 Claims, 4 Drawing Sheets

AGGLUTINATION REACTION DEVICE HAVING GEOMETRICALLY MODIFIED CHAMBERS

This application is a continuation of application Ser. No. 07/614,817, filed Nov. 16, 1990 now abandoned which is a continuation in part of Ser. No. 07/138,256 filed Dec. 23, 1987 now abandoned.

BACKGROUND OF THE INVENTION

The present invention is directed to an improved device for performing an agglutination reaction of immunochemical particles. The agglutination reaction device is designed to provide a convenient means for performing and reading the results of an agglutination reaction. A particular improvement involves varying the geometry, namely the width and/or depth, of a portion of the path along which liquid in the device flows by capillary action.

Agglutination reactions and their procedures are generally well known in the art. A typical agglutination reaction consists of the clumping together (or aggregation) in suspension of antigen- or antibody-bearing cells, microorganisms, or particles in the presence of specific analytes. This clumping or agglutination of particles is then monitored to determine the absence or presence of an analyte sought to be detected.

One method for reacting immunochemical particle reagents involves placing liquid reagents on a glass slide and generally rocking or swirling the slide back and forth to cause the reagents to mix and form agglutinations. Methods have also been developed to avoid the necessary swirling of the particle reagents in order to visualize the agglutinations. For example, U.S. Pat. No. 4,596,695 discloses an agglutination reaction chamber for reacting immunochemical particle reagents. The chamber includes a first transparent panel having a first surface and a second panel having a second surface spaced apart from the first surface to define a chamber inbetween. The chamber intrinsically causes immunochemical particle reagents to flow by capillary action without an external motion imparted to the chamber during which flow the immunochemical particle reagents can react.

An object of the present invention is to provide a device that can be easily adapted for use in the automated diagnosis of a plurality of samples. Another object of the present invention is to provide a device capable of performing multiple, highly sensitive, diagnostic tests simultaneously on a single sample in a single device. In one aspect, the present invention is directed to a device in which the agglutination reaction can be rapidly performed and monitored with a minimum of sample material. In another aspect, the present invention is directed to a device having multiple channels radiating from a central well where multiple reactions on a single sample can be rapidly performed and monitored with a minimum of sample material with the results of such reactions being easily, visibly observable. In another aspect, the present invention is directed to devices for performing agglutination reactions having enhanced performance properties through utilization of a means for controlling the flow of liquid through the reaction chamber of the performance properties through utilization of a means for controlling the flow of liquid through the reaction chamber of the device, namely, through modification of the geometric configuration of the agglutination reaction chamber or the internal shape of the chamber so as to provide a non-random patterned array of aggregated agglutinates which non-random pattern is more easily observable than agglutinates aggregated in a random array.

SUMMARY OF THE INVENTION

The present invention provides a device for performing agglutination reactions comprising: in adherent relationship, a first wettable layer, a second liquid-occlusive layer parallel to and overlying the first layer, and a third layer parallel to and overlying the second layer and having a window for observing particles. The second layer is interposed between, and is in adherent relationship to, the first and third layers. The second layer has at least one general slot therein defining a channel for directing liquid conducted by capillary action through a chamber defined by the slot in conjunction with the first and third layers. Agglutination reactions can be performed in the chamber. The chamber has a proximate zone and a distal zone. The aforesaid slot in the second layer defines at least approximately parallel walls in the proximate zone thereby defining a first path of approximately constant width. The aforesaid slot in the second layer also defines walls in the distal zone which are spaced to define a second path of increased width compared to the first path. This arrangement of such different paths in the chamber at least in part enables agglutination reactions in the chamber to result in the formation of a surprisingly non-random pattern of aggregated particles in the distal zone of the chamber. Such a non-random pattern is more readily observable through the third layer than if a random pattern of aggregated particles occurred instead.

The present invention also provides in particular for such a device for performing agglutination reactions in which the second layer has at least one general slot therein defining a channel for directing liquid conducted by capillary action through a chamber defined by the slot and by the first and third layers and within which chamber agglutination reactions can be performed. The chamber has a proximate zone and a distal zone. The slot in the second layer defines walls in the proximate zone which with the first and third layers define a first path of approximately constant depth. The slot in the second layer also defines walls in the distal zone which with the first and third layers define a second path of increasing depth compared to the first path whereby agglutination reactions in the chamber result in the formation of a non-random pattern of aggregated particles in the distal zone of the chamber which non-random pattern is more readily observable through the window of the third layer than if a random pattern of aggregated particles occurred instead.

Additionally, the present invention provides a device for performing simultaneously a plurality of agglutination reactions. The device comprises: in adherent relationship, a first wettable layer, a second liquid-occlusive layer parallel to and overlying the first layer, and a third layer parallel to and overlying the second layer and having windows for observing particles. The second layer is interposed between and is in adherent relationship to the first and third layers. The general slot of the second layer has a plurality of slotted arms (also slots) in radial spatial relationship to each other. These radiating slots respectively define channels for directing liquid conducted by capillary action through chambers respectively defined by the slots in conjunction with the first and third layers. Agglutination reactions can be performed simultaneously in these chambers. Each of the chambers has a proximate zone and a distal zone, and each of the slots defines at least approximately parallel walls in the corresponding proximate zone thereby defining a corresponding first path of approximately constant width and defines walls in the corresponding distal zone which are spaced to define a corresponding second path of increased width compared to the first path. Agglutination reactions performed in the corresponding chambers can result in the formation of a non-random pattern of aggregated particles in the distal zone of each chamber which non-random pattern is more readily observable through the window of the third layer than if a random pattern of aggregated particles occurred instead.

An agglutination reaction device of the present invention additionally can include a sample receiving well contiguous with the ingress of the agglutination chamber.

In an agglutination reaction chamber of the present invention, the reagent can be present in dried spots or strips. It is also possible to suspend the reagent in a water-soluble polymer.

A copending U.S. patent application, Ser. No. 07/138,253, filed on Dec. 23, 1987, entitled "Agglutination Reaction Device" (the disclosure of which is hereby specifically incorporated herein by reference), teaches an agglutination reaction chamber which is constructed to be very small in size to accommodate automated and efficient use of sample and reagents. Typically, the length of such a chamber is from about 10 to about 75 millimeters (mm), the channels are from about 0.01 to about 5.0 mm in depth and from about 0.1 to about 10.0 mm in width. A typical overall size for such an agglutination reaction device having four chambers and a sample receiving well is about 37.5 mm × 12.5 mm × 1.5 mm (l × w × h).

The aforesaid copending United States Patent Application also generally discloses a means for controlling the flow of fluid in an agglutination reaction chamber involving the configuration of the channel or geometric formations within the channel such as ridges, particularly ridges formed in the channel which extend across the entire width of the channel and for at least a portion of the length of the channel. The aforesaid copending United States Patent Application also discloses another means for controlling the flow of fluid in the chamber, namely utilization of a water-soluble material, such as a water-soluble polymer, (e.g., polyvinylpyrrolidone, polyvinylalcohol, gelatin, or bovine serum albumin) dried in portions of the channel.

However, it has been found that such expedients, while useful in helping to control the overall rate of liquid (fluid) flow in the channels, can be difficult to employ so as to obtain consistently uniform results. It has recently been found, and is the subject of a United States Patent Application entitled "Improved Agglutination Reaction Device Utilizing A Porous Absorbent Material", and filed event date herewith, that a porous, absorbent material such as an absorbent paper utilized as the fluid flow control means provides advantages in both manufacturing and performance over the utilization of coatings of water-soluble materials such as polyvinylpyrrolidone (PVP). For example, where a water-soluble polymer such as polyvinlypyrolidone is utilized, it has been found that it can be difficult to obtain dried coatings of the polyvinylpyrrolidone so as to obtain consistent stability of overall flow of liquid in the channels.

The present invention is directed to devices for performing agglutination reactions having improved properties including improved means for controlling the rate of liquid flow per unit area through the agglutination chamber so as to produce a non-random pattern of aggregated agglutinated particles. The present invention also is directed to such devices constructed in the form of convenient, disposable structures, such as disposable, laminated cards, optionally mounted in disposable rigid containers.

DETAILED DESCRIPTION OF THE PREFERRED EMBODIMENTS

The present invention is directed to improved devices suitable for performing agglutination reactions. Surprisingly, it has been found that the devices of the present invention, for performing agglutination reactions, provide enhanced properties over prior art devices. The devices of the present invention utilize a means for controlling the rate of flow per unit area of liquid through the reaction chamber of the device. In particular these means consist of modifying the geometric configuration of the chamber or the internal shape of the chamber as illustrated in FIGS. 1, 2, 3, 4, 5 and 6.

Figure 1:
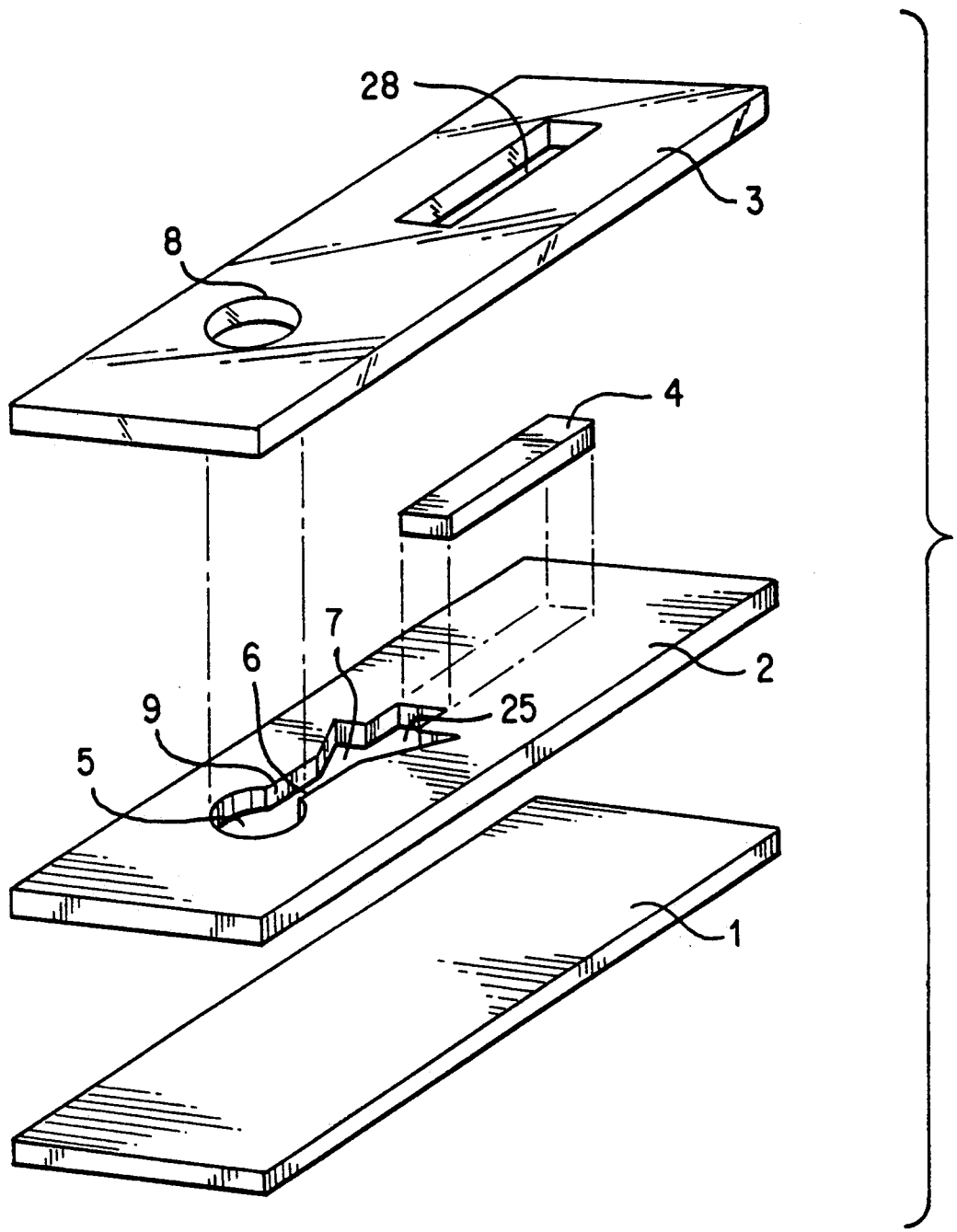
FIG. 1 is an exploded, top perspective view of an embodiment showing a three layer structure comprising a first or base layer, a second layer showing a cutout for a round receiving well and an agglutination chamber having a flared portion at its distal end, a strip of porous absorbent material, and a third or top layer.

FIG. 1 represents an embodiment of a device for performing agglutination reactions according to the invention. This embodiment has, in adherent relationship, a first wettable, but liquid-occlusive, layer (1), a second liquid-occlusive layer (2) parallel to and overlying the first layer (1), and a third liquid-occlusive, preferably non-wettable, layer (3) parallel to and overlying the second layer (2) and having a window, or viewing area, for observing particles. The first layer (1) is made of a liquid-occlusive material having a water-wettable surface. In this embodiment the third layer (3) is made from a clear, liquid-occlusive, non-wettable, film, such as a clear polycarbonate film, and therefore also serves as a window, or viewing area, for observing particles in the agglutination chamber. The second layer (2) is interposed between, and is adhered to, the first layer (1) and third layer (3), for example by means of an adhesive on each side of layer (2) facing the topside of the first layer (1) and the underside of the third layer (3) respectively. The second layer (2) has a general slot (25) cut through its thickness defining a channel for directing liquid for conduction by capillary action through the chamber defined by the slot (25) in conjunction with the first layer (1) and third layer (3) respectively.

In other words, when the first, second and third layers are laminated together, a portion of each of the first and third layers serve respectively as the floor and roof of the agglutination chamber with part of the walls of the slot (25) of the second layer (2) defining the walls (9) of the chamber. The agglutination reaction chamber has a proximate zone (6) and a distal zone (7), which proximate zone (6) is represented by the generally rectangular portion of the slot (25) of the second layer (2) with the distal zone (7) being represented by the deltoid or flared portion of the slot (25) of the second layer (2).

The embodiment illustrated by FIG. 1 has a well-defining slot (8) in the third layer (3) and a corresponding second well-defining slot (5) in the second layer (2) of the same size and configuration as the well-defining slot (8) in the third layer (3). The well-defining slot (5) in the second layer (2) is positioned directly below the well-defining slot (8) in the third layer (3) such that when all three layers are laminated together, the second well-defining slot (5) in conjunction with the well-defining slot (8) along with the corresponding portion of the first layer define a well for receiving liquid, the well being in liquid communication with the proximate zone (6) of the chamber. The bottom of the well is formed from a corresponding circular portion of the first layer (1) which portion can be considered to be the projection of the outline of slots (5) and (8) onto the surface of layer (1).

In the embodiment illustrated by FIG. 1, the overall rate of liquid flow through the agglutination chamber is controlled by means of a strip of porous absorbent material (4), preferably filter paper, in liquid communication with the chamber and positioned adjacent to the distal end of the chamber, and preferably extending partially into the distal end of the chamber, when the structures of FIG. 1 are laminated respectively together. As used in the present specification, the absorbent porous material, for example paper, is to be distinguished from water-soluble materials such as dried coatings of water-soluble polymers such as polyvinylpyrrolidone, polyvinylalcohol, gelatin, or bovine serum albumin. The porous absorbent material utilized in present invention is itself generally not water-soluble. In a more preferred embodiment, layer (3) as shown in FIG. 1 has a slot (28), of slightly larger dimensions as the strip of porous paper (4), such that when the respective layers are adhered together, the strip of porous absorbent material (4) lies partially within the slot (28), more particularly so that a front minor portion of the strip (4) lies within the distal zone (7) of the slot (25) with the remaining major portion of the strip lying within slot (28), so as to prevent disadvantageous formation of microcapillary channels at the sides of and along the length of the strip (4). The resulting laminated structure, can be thought of as being in the form of a thin, disposable card with the paper strip (4) being in liquid communication with the distal zone (7) of the agglutination chamber.

For example, when a solution of cells is introduced into the receiving well of a device of the invention, which well is in liquid communication with the proximate end of the reaction chamber; and the chamber contains antibodies directed against antigens on the cells and which antigens are dried onto the floor of the chamber, the solution will migrate through the chamber by capillary action, mix with the antisera, and the cells will aggregate. This will all occur without any centrifugation or mixing steps. Control of the overall rate of flow of the liquid through the channel is necessary because the agglutination reaction occurs preferably during the period of liquid flow. Sufficient incubation time is built into the period of liquid flow to achieve optimum reaction of the reagents.

Figure 2:
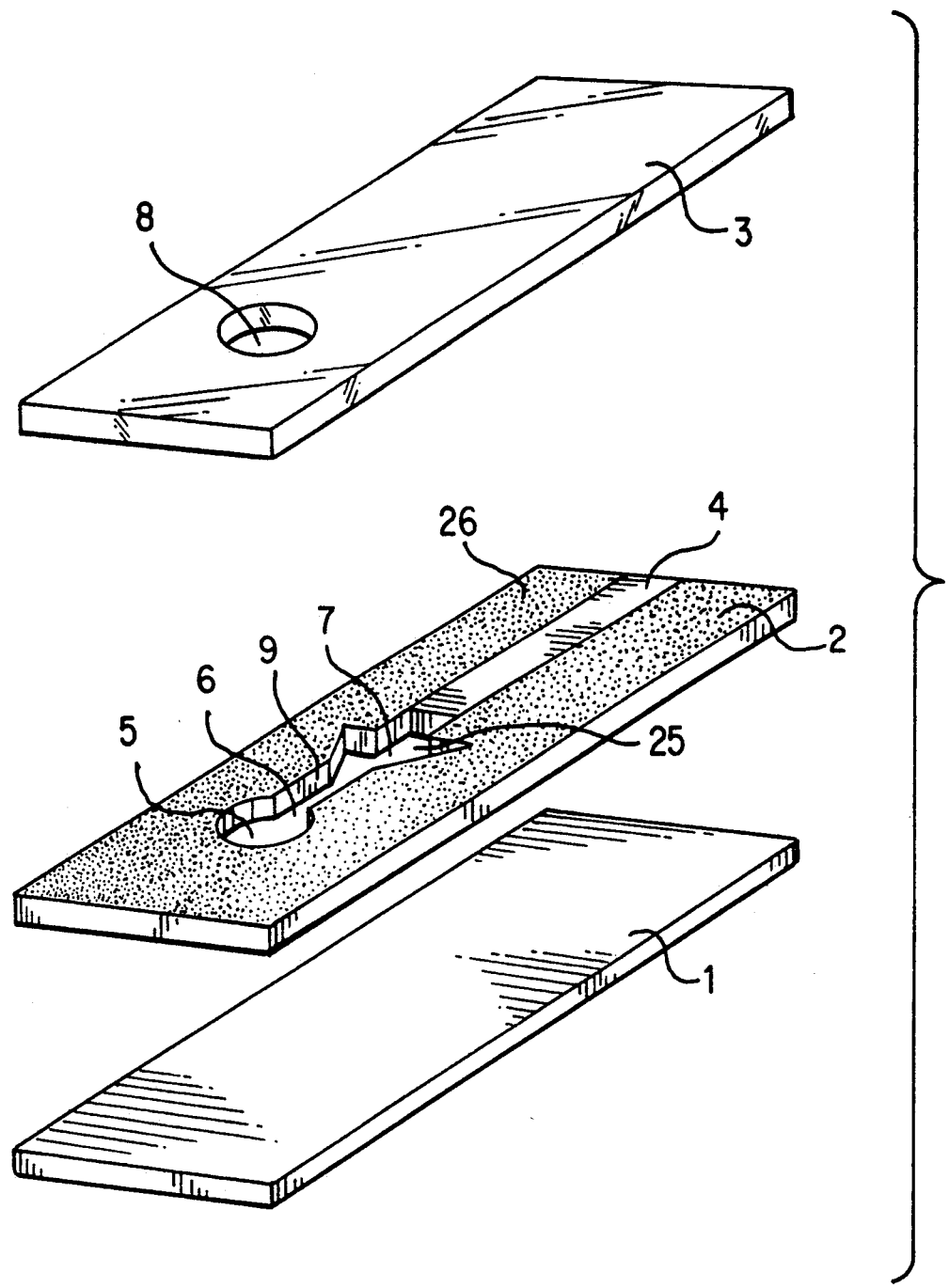
FIG. 2 is an exploded, top perspective view of another embodiment showing a three layer structure comprising a first or base layer, a second layer showing a cutout for a round receiving well and an agglutination chamber having a flared portion at its distal end with an integral porous absorbent strip in the second layer at the distal end of the chamber, and a third or top layer.
Figure 3:
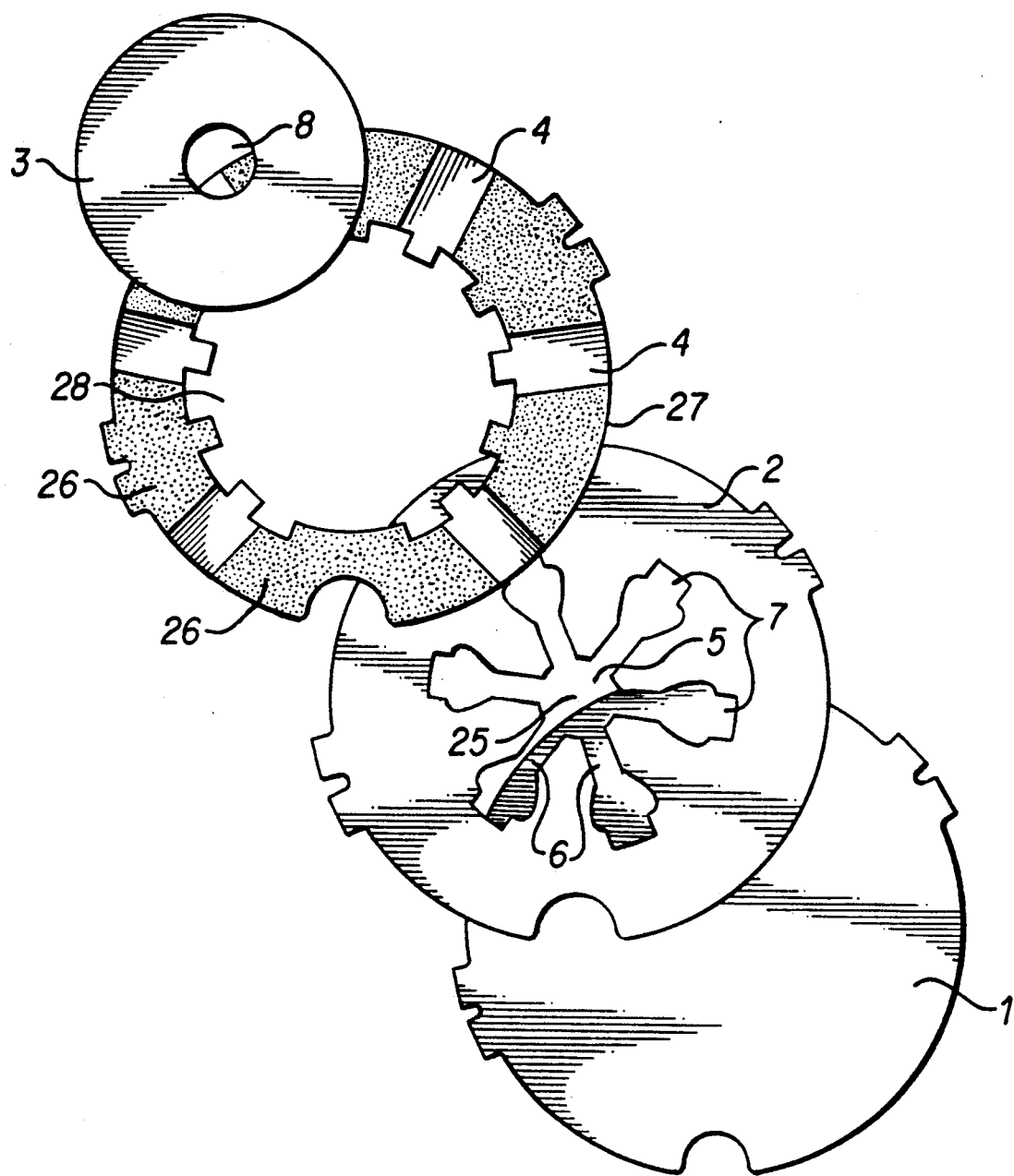
FIG. 3 is a top plan view of another embodiment showing the parts of a laminated structure comprising a base layer, a second layer having a cutout for a round receiving well and multiple radiating agglutination chambers having flared distal zones, an annular structure (ring) having alternating liquid absorbent regions (4) and liquid-occlusive regions (26), and another round layer which in cooperation with the annular structure forms the top layer.
Figure 4:
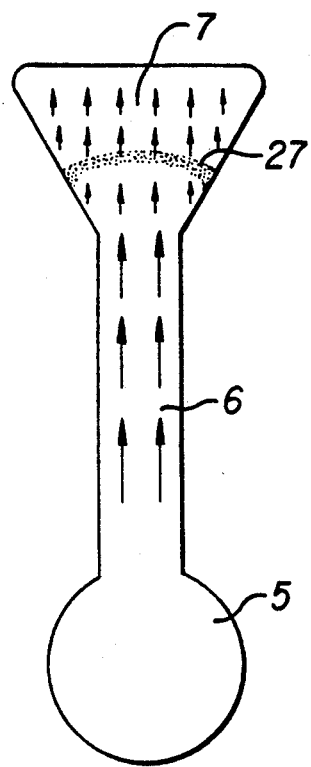
FIG. 4 is a schematic diagram illustrating regions of different flow rate per unit area outward from the receiving well for an agglutination chamber having a flared distal end, and illustrating a band of agglutinated particles in the flared distal end.

In FIGS. 1, 2, and 3, the general slot (25) in layer (2) defines at least approximately parallel walls (9) in the proximate zone (6) of the chamber thereby defining a first path of approximately constant width. Looking in the direction toward the distal end of the chamber, the general slot (2) defines walls in the distal zone (7) which are spaced to define a second path of increased width compared to the first path of the proximate zone (6). It has been found that agglutination reactions performed in such a chamber advantageously can result, surprisingly, in the formation of one or more patterned formations, such as, for example bands, of agglutinated particles in the distal zone (7) of the chamber which patterns are more easily observable through the window of the third layer (3) than non-patterned aggregates of agglutinated particles which generally result in agglutination chambers of the prior art. FIG. 4 shows a schematic representation of an approximately semicircular band (27) of agglutinated particles in the zone of increasing chamber width, namely in the flared (here approximately deltoid-shaped) "second path" of the chamber in the distal zone (7) of the chamber. As represented in schematic form in FIG. 4 through the use of arrows of different length along the reaction path in the chamber, the walls in the distal zone (7) are spaced to provide a decreased liquid flow rate per unit area of liquid path along this second path. In FIG. 4, the shorter arrows are, of course, intended to represent smaller flow rate per unit area of path, compared to that represented by the longer arrows.

Figure 5:
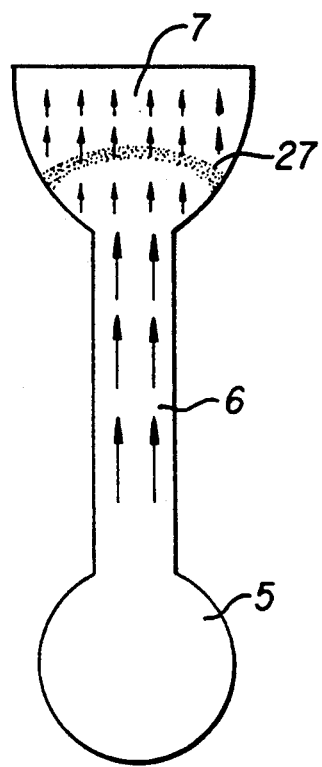
FIG. 5 is a schematic diagram illustrating regions of different flow rate per unit area outward from the receiving well for an agglutination chamber having a semicircular, or bowl-shaped, distal end, and illustrating a band of agglutinated particles in the semicircular end.
Figure 6:
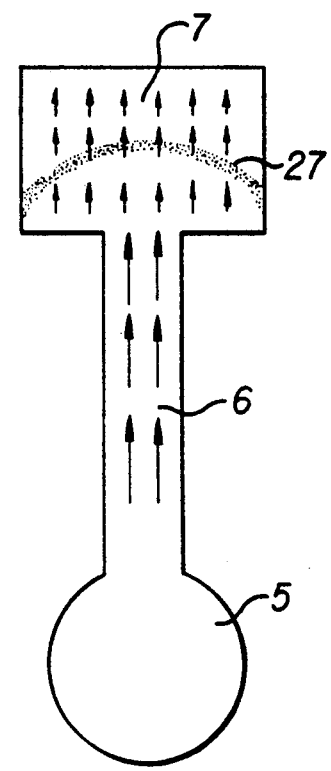
FIG. 6 is a schematic diagram illustrating regions of different flow rate per unit area outward from the receiving well for an agglutination chamber having an approximately rectangular shape.

While deltoid-shaped configurations of the second path of the distal zone in the chambers is preferred, it has been found that other geometric configurations for this so-called "second path" provide advantageous patterned formations of agglutinated particles. For example, the side walls in the second path can be formed to be convex giving an approximately semicircular or bowl-shaped configuration to the second path as illustrated in FIG. 5. Alternatively, although less preferred, the side walls of the second path can be formed to provide a second path with an approximately rectangular shape as illustrated in FIG. 6.

FIG. 2 represents another embodiment of a device, in the form of a laminated card when the layers shown in FIG. 2 are adhered together, for performing agglutination reactions. This embodiment has, in adherent relationship, a first wettable, but liquid-occlusive, layer (1), a second layer (2) parallel to and overlying the first layer (1), and a third liquid-occlusive, preferably non-wettable, layer (3) parallel to and overlying the second layer (2) and having a window, or viewing area, for observing particles. The first layer (1) is made of a liquid-occlusive material having a water-wettable surface. As in the embodiment represented by FIG. 1, this embodiment also utilizes a third layer (3) made from a clear, liquid-occlusive, preferably non-wettable film, such as a clear polycarbonate film or a non-wettable cellophone tape, which therefore also serves as a window for observing particles in the agglutination chamber. The second layer (2) is interposed between, and is adhered to, the first layer (1) and third layer (3), for example by means of an adhesive on each side of layer (2) facing the topside of the first layer (1) and the underside of the third layer (3) respectively. The second layer (2) has a general slot (25) cut through its thickness defining a channel for directing liquid for conduction by capillary action through the chamber defined by the slot (25) in conjunction with the first (1) and third (3) layers respectively.

As in the embodiment represented by FIG. 1, when the first, second and third layers are laminated together, a portion of each of the first and third layers serve respectively as the floor and roof of the agglutination chamber with part of the walls of the slot (25) of the second layer (2) defining the walls (9) of the chamber, the other part of the walls of slot (25) defining the walls of the circular receiving well (5). The agglutination reaction chamber has a proximate zone (6) and a distal zone (7), which proximate zone (6) is represented by the generally rectangular portion of the slot (25) of the second layer (2) with the distal zone (7) being represented by the deltoid or flared portion of the slot (25) of the second layer (2).

Each of the embodiments illustrated by FIGS. 1 and 2 has a well-defining slot (8) in the third layer (3) and a corresponding second well-defining slot (5) in the second layer (2) of the same size and configuration as the well-defining slot (8) in the third layer (3). The well-defining slot (5) in the second layer (2) is positioned directly below the well-defining slot (8) in the third layer (3) such that when all three layers are laminated together, the second well-defining slot (5) in conjunction with the well-defining slot (8) along with the corresponding portion of the first layer define a circular well for receiving liquid, the well being in liquid communication with the proximate zone (6) of the chamber. The bottom of the well is formed from a corresponding circular portion of the first layer (1).

However, in the embodiment of FIG. 2 the second layer (2) is made of a liquid absorbent material, such as absorbent paper, selectively impregnated through its thickness with a substance, such as a water-repellent ink, to form an impregnated region (26) and a non-impregnated region (4). The non-impregnated region (4) is liquid absorbent and the impregnated region (26) is liquid-occlusive. In this embodiment, the non-impregnated region (4) which is in liquid communication with the distal zone (7) of the chamber serves as means for controlling the overall rate of liquid flow through the agglutination chamber. The second layer (2) also has a slot (25) in the impregnated region (26) defining a channel for directing liquid conducted by capillary action through a chamber defined by the slot (25) in conjunction with the first layer (1) and third layer (3). This chamber also has a proximate zone (6) and a distal zone (7). It is within this chamber that agglutination reactions can be performed. As can be seen from FIG. 2, the non-impregnated region (4) is located adjacent to the distal end of the agglutination chamber and is in liquid communication with the chamber.

FIG. 3 illustrates an exploded, plan view of a preferred embodiment of the invention. This embodiment provides for performing a plurality of agglutination reactions utilizing a minimal amount of liquid sample. The device in assembled form can be thought of a relatively thin, laminated, disposable card having in this particular illustration six agglutination chambers radiating from a common liquid receiving well. The device of FIG. 3 comprises, in adherent relationship, an approximately circular first wettable but liquid-occlusive layer (1), an approximately circular second liquid-occlusive layer (2) parallel to and overlying the first layer (1), and a third liquid-occlusive layer (3) parallel to and overlying the second layer (2). These respective layers can be bonded together, for example, by means of an adhesive between the respective layers. In this embodiment the third layer (3) is made of a circular clear plastic film, such as a polycarbonate film, thereby providing windows, or viewing areas, for observing particles in the six radiating agglutination chambers. The second layer (2), interposed between and in adherent relationship to the first and third layers has a slot (25) in the form of a central, circular portion (5) having six radial, slotted arms extending outward therefrom. These radial arms of the slot (25) define six channels for directing liquid conducted by capillary action through chambers respectively defined by the radial, slotted arms in conjunction with the first layer (1) and the third layer (3). Within the resulting six chambers agglutination reactions can be performed simultaneously. Each of the six chambers has a generally rectangular proximate zone (6) and a generally flared or deltoid shaped distal zone (7). The overall rate of liquid flow through each agglutination chamber in this embodiment is controlled by means of a strip of porous absorbent material (4), preferably filter paper, projecting from a generally annular ring (27) of such porous material, into the distal zone (7) of each of the channels defined by the radial, slotted arms. The annular ring (27) is selectively impregnated through its thickness with a substance to provide alternating non-impregnated liquid absorbent regions (4) and impregnated liquid-occlusive regions (26). These non-impregnated strips (4) of paper projecting from the annular ring (27) are in liquid communication with the chambers and are positioned adjacent to the distal ends of the chambers, preferably positioned partially in the distal ends, when the structures of FIG. 3 are laminated respectively together.

The third layer (3) of the device represented by FIG. 3 has a circular well-defining slot (8), and the second layer has a corresponding circular second well-defining slot (5) of the same size and configuration as the well-defining slot (8) in the third layer (3). The well-defining slot (5) of the second layer (2) is positioned directly below the well-defining slot in the third layer (3) in the assembled configuration. Thus the second well-defining slot (5) in conjunction with the well-defining slot (8) in the third layer (3) and the respective circular portion of the first layer (1) define a well for receiving liquid, the well being in liquid communication with the proximate zone (6) of each of the chambers.

The resulting, generally circular laminated structure, can be thought of as being in the form of a relatively thin, disposable card with the fluid-absorbent paper strip (4) being in liquid communication with the distal zone (7) of the agglutination chamber.

If desired, the flow rate per unit area in the distal zone of the reaction chamber of an embodiment of the invention can be gradually decreased along the general direction of flow by gradually increasing the space between the floor and the roof of the chamber along the direction of liquid flow, for example by gradually bowing the roof of the chamber in the distal zone upward and/or by gradually bowing the floor of the chamber in the distal zone downward. It has been found that such modification of the space between the floor and the roof of the chamber in the distal zone of the chamber can also contribute to the formation of regular patterns of agglutinated particles being formed in the distal zone of the chamber. For example, the space between the floor and the roof of the chamber can be gradually increased by stamping a spherical dome-shaped or cylindrical dome-shaped configuration in an area of the third layer (3) in such manner that when the third layer is adhered to the second layer (2) the dome in the third layer overlies the distal zone of the reaction chamber. Another example of a way to provide a gradually increasing space between the floor and the roof of the distal zone of the reaction chamber is to stamp a spherical bowl-shaped or cylindrical bowl-shaped depression in the base or first layer (1) in such manner that when the first layer (1) is adhered to the second layer (2) the bowl-shaped depression occurs in the floor of the distal zone of the reaction chamber.

All types of agglutination-based assays can be accommodated with a device according to the present invention. In some instances, a soluble reagent can be dried as spots or strips in the reaction chamber, for example, in blood typing. In other instances, a particulate reagent, such as a latex reagent, can be dried in the chamber. In yet another approach, a reagent can be dispersed in a solution which is placed in the chamber. One preferred reagent solution is microparticulates in a solution of dextran and sucrose. Preferably, the microparticulate reagent is mixed in a solution of about 2.5 to about 5.0 percent by weight dextran and from about 15 to about 20 percent by weight sucrose. Another preferred solution for mixing reagents is FICOLL (a trademark by Sigma Chemical Co., St. Louis, Mo. for a nonionic synthetic polymer of sucrose) from about 20 to about 30 percent by weight. Also, depending on the requirements of the assay, the flow of the liquid through the chamber can be controlled as described above to accommodate any necessary incubation times and assay sequences.

A particularly advantageous feature of the present invention is that it provides for the ability to simultaneously perform multiple assays while utilizing a very small amount of sample material, for instance, a single drop. Also, the agglutination assay is essentially self-performing once the drop has been added to the agglutination reaction device. It is important to note that by utilizing means for controlling the rate of flow per unit area of liquid through the reaction chamber, particularly through the distal zone of the chamber, of a device according to the present invention, namely by modification of the geometric configuration of the distal zone of the chamber or the internal shape of the chamber as discussed above, additional enhanced results can be obtained such as enhanced observability of aggregates of agglutinated particles in the distal zone of the reaction chamber.

A device of the invention is suitable for use in an automated fashion where the agglutination reaction can be monitored by an optical scanner. For example, the construction of the agglutination reaction device enables one to use an image analysis system available from Olympus (CUE-2, Lake Success, N.Y.) to determine the quantity and concentration of agglutinated material. The agglutination reaction device is illuminated, such that transmitted or reflected light can be read by the reader. The image is then computer analyzed to determine the quantity of agglutination which has occurred and to enhance the image for very accurate and sensitive determinations. By confining the sample to a chamber such as formed in the agglutination reaction device, there is no problem with curvatures of droplets or water which could interfere with the image seen by the reader. Thus, the uniformity of the reacted sample and reagents achieved by the agglutination reaction device provides an excellent imaging format for a reader or other imaging devices. Besides being able to read the transmission of light through the bottom of the agglutination reaction device, it is also possible to read reflected light because the sample and reacted reagents are confined to capillary chambers formed by the agglutination reaction device.

It is required that a surface, preferably the bottom surface, of an agglutination chamber of the present invention be hydrophilic or wettable such that capillary flow is induced when a sample is placed in contact with the ingress of the proximate zone of the chamber. This can be accomplished by using a hydrophilic or water-wettable material for the surface. However, it is also possible to chemically treat or coat otherwise non-wettable (hydrophobic) materials such that they become wettable. This preparation of a wettable surface can also be used to influence the flow rate in the capillary chamber.

Suitable materials for preparing a wettable layer for various embodiments of the invention include, for example, cellulose acetate butyrate, a wettable nylon material, or a layer coated with an acrylic latex emulsion to render the surface water-wettable. The "roof" of an agglutination chamber of the invention may be either wettable or non-wettable.

The small size of the reaction devices of the invention allows for the rapid and convenient handling of a plurality of devices and therefore samples. A device can then be loaded into an automated apparatus which indexes and scans the individual channels for the assay result and records this information for future access. The small dimensions of the agglutination reaction device also provide for efficient use of sample and reagents.

The following examples are provided to further illustrate embodiments of the invention and should not be construed as a limitation on the scope of the invention.

EXAMPLE 1

Laminate disposable cards were prepared by assembling together a wettable base layer, a die cut adhesive core layer, paper strip assemblies, and a clear polycarbonate top assembly as shown in FIG. 1. To prepare the wettable base layer, 1 mil thick nylon film (Capran Emblem 2500, Allied Signal, Morristown, N.J.) was first laminated onto a paperboard backing (Westvaco Hi Yield PrintKote, 16 mil, New York, N.Y.) through the use of a two-sided adhesive layer (Fasson Fastape A, Fasson Specialty Division, Avery, Painesville, Ohio). Base subassemblies (3"×6", i.e., 3 inches×6 inches) were cut from this material, using care to keep the exposed nylon surface clean. Steel rule dies were prepared to cut the channel shapes as shown in FIG. 1 from a second sheet of two-sided adhesive (3.1 mil, Specialty Tapes, Division of RSW Inc., Racine, Wis.) which has release liner on both adhesive surfaces. One piece of release liner was removed from the die-cut part and this adhesive layer was placed onto the nylon surface of the base subassembly. Pieces of filter paper (2.5×19 millimeter, 1CHR, Whatman, Clifton, N.J.) which have a layer of one-sided adhesive (ARCare 7597, Adhesive Research, Glen Rock, Pa.) laminated to one surface were positioned on the base/core subassemblies with the one-sided adhesive away from the card. Finally, a sheet of clear polycarbonate film (GE Part 8040-112, Cadillac Plastics, Evansville, Ind.) was die-cut as shown in item (3) of FIG. 1, and laminated onto the Base/core/paper subassembly using a mechanical laminator set at 50 psi and 0.2 ft/sec.

EXAMPLE 2

Laminate disposable cards were prepared using a 3"×6" piece of paperboard coated with a wettable acrylic latex emulsion coat (Part 150HT(26-1), Daubert Coated Products, Dixon, Ill.) in place of the nylon base subassemblies described in Example 1. Die-cut core layers were prepared using 3.1 mil two-sided adhesive (ARCare 7580, Adhesive Research, Glen Rock, Pa.). All other steps in card assembly were identical to those of Example 1.

EXAMPLE 3

Fixed human erythrocytes (Duracytes ™, Abbott Laboratories, North Chicago, Ill.) were coated with affinity purified goat antibodies directed against Hepatitis B surface antigen (HBsAg) at a final concentration of 100 ug/ml (micrograms/milliliter) in the presence of 0.05% (weight/volume) chromic chloride in 0.1M (Molar) acetate buffer at a pH of 4.0. These cells were overcoated with 1% (weight/volume; w/v) human serum albumin (Sigma Chemical Co., St. Louis, Mo.) in 25 mM (millimolar) Tris-HCl (pH=7.4) buffer and then resuspended with 0.1% bovine serum albumin (BSA) (Sigma Chemical Co., St. Louis, Mo.) in phosphate buffered saline (pH=7.4) containing 5% (volume/volume) normal goat serum at a final cell concentration of 10% (volume/volume). Serum samples (20 ul; i.e., 20 microliter) containing either 0, 6.25, or 25 ng/ml (nanograms/milliliter) of HBsAg were mixed with 10 ul (microliter) aliquots of these coated Duracytes and the solution was immediately added to the sample addition well of laminate disposable cards prepared as described in Example 1. The solutions flowed rapidly through the capillary channel (1-2 seconds; sec) and then slowly flowed into the paper strips. It took approximately 7 minutes for the liquid to completely saturate the paper strip. After the paper strips had completely wetted, agglutinated reaction products of the Duracyte cells could be observed within certain of the capillary channels of the laminate disposable cards. Duracytes which had been mixed with samples containing HBsAg aggregated, whereas the duracytes which were mixed with sera which did not contain HBsAg, did not aggregate.

EXAMPLE 4

Laminate disposable cards were prepared as described in Example 2 with a flared channel design as shown in FIG. 1. Duracytes coated with anti-HBsAg (Example 3) were mixed with sera containing various concentrations of HBsAg and were introduced into the laminate disposable cards having flared channels. After 5 minutes, aggregated particles appeared and formed into an easily visible band of agglutinates which stretched across the flared portion of the channel as shown in FIG. 4. In channels where there was not any HBsAg present, the Duracytes did not aggregate and no band of cells was visible.

What is claimed is:

1. A device for performing agglutination reactions comprising: in adherent relationship, a first hydrophilic layer, a second liquid-occlusive layer parallel to and overlying said first layer, and a third layer parallel to and overlying said second layer and having a transparent opening for observing particles during an agglutination reaction, said second layer interposed between and in adherent relationship to said first and third layers, said second layer having at least one slot therein defining a channel for directing liquid conducted by capillary action through a chamber defined by said slot and by said first and third layers and within which chamber agglutination reactions can be performed, said chamber having a proximate zone and a distal zone, said proximate zone comprising a well for receiving a liquid, said liquid flowing to the distal zone of the chamber, said slot defining at least approximately parallel walls in said proximate zone thereby defining a first path of approximately constant width and defining walls in said distal zone which are spaced to define a second path of increased width compared to said first path whereby agglutination reactions in said chamber result in the formation of a non-random pattern of aggregated particles in said distal zone of said chamber which non-random pattern is visibly observable through said transparent opening of said third layer, and wherein said chamber has a porous absorbent material in liquid communication with said chamber for controlling overall rate of liquid flow through said chamber said porous absorbent material being positioned partially within said second path toward the outer perimeter of said second path in said distal zone along the direction of liquid flow in said first path wherein at least a portion of the porous absorbent material is positioned partially within said distal zone of said chamber, and wherein no portion of said porous absorbent material is in contact with said proximate zone of said chamber and no portion of said porous absorbent material is positioned preceding said proximate zone of said chamber along the direction of liquid flow in said chamber.

2. The device of claim 1 wherein said third layer is hydrophobic.

3. The device of claim 1 wherein said slot defines walls in said distal zone which are spaced from each other such that agglutination reactions in said chamber result in bands of particles being approximately semicircular in configuration.

4. The device of claim 1 wherein said slot defines walls in said distal zone which are spaced to provide a decreased flow rate per unit area of liquid along said second path.

5. The device of claim 1 wherein said slot defines walls in said distal zone which are spaced to provide said second path with an approximately rectangular shape.

6. The device of claim 1 wherein said porous absorbent material comprises a cellulosic material.

7. The device of claim 6 wherein said cellulosic material comprises paper.

8. The device of claim 1 in which said third layer contains a well-defining slot and said second layer contains a corresponding second well-defining slot of the same size and configuration as said well-defining slot in said third layer and positioned directly below said well-defining slot in said third layer, wherein said second well-defining slot in conjunction with said well-defining slot in said third layer and said first layer define a well for receiving liquid, said well being in liquid communication with said proximate zone of said chamber.

9. The device of claim 8 wherein said third layer is hydrophobic.

10. The device of claim 1 wherein said walls in said distal zone are outwardly diverging from each other to provide said second path with an outwardly flared configuration relative to said first path.

11. The device of claim 10 wherein said outwardly diverging walls are approximately deltoid in shape.

12. The device of claim 10 wherein said outwardly diverging walls are approximately semicircular in shape.

13. A device for performing agglutination reactions comprising: in adherent relationship, a first hydrophilic layer, a second liquid-occlusive layer parallel to and overlying said first layer, and a third layer parallel to and overlying said second layer and having a transparent opening for observing particles during an agglutination reaction, said second layer interposed between and in adherent relationship to said first and third layers, said second layer having at least one slot therein defining a channel for directing liquid conducted by capillary action through a chamber defined by said slot and by said first and third layers and within which chamber agglutination reactions can be performed, said chamber having a proximate zone and a distal zone, said proximate zone comprising a well for receiving a liquid, said liquid flowing to the distal zone of the chamber, said slot defining walls in said proximate zone which with said first layer define a first path of approximately constant depth and defining walls in said distal zone which with said first layer define a second path of increasing depth compared to said first path whereby agglutination reactions in said chamber result in the formation of a non-random pattern of aggregated particles in said distal zone of said chamber which non-random pattern is visibly observable through said window of said third layer, and wherein said chamber has a porous absorbent material in liquid communication with said chamber for controlling overall rate of liquid flow through said chamber said porous absorbent material being positioned partially within said second path toward the outer perimeter of said second path in said distal zone along the direction of liquid flow in said first path wherein at least a portion of the porous absorbent material is positioned partially within said distal zone of said chamber, and wherein no portion of said porous absorbent material is in contact with said proximate zone of said chamber and no portion of said porous absorbent material is positioned preceding said proximate zone of said chamber along the direction of liquid flow in said chamber.

14. The device of claim 13 wherein said path of increasing depth in said distal zone is provided by a domed depression in said third layer looking along the direction of liquid flow in said second path.

15. The device of claim 13 wherein said path of increasing depth in said distal zone is provided by a depression in said first layer looking along the direction of liquid flow in said second path.

16. The device of claim 13 wherein said third layer is hydrophobic.

17. A device for performing simultaneously a plurality of agglutination reactions comprising: in adherent relationship, a first hydrophilic layer, a second liquid-occlusive layer parallel to and overlying said first layer, and a third layer parallel to and overlying said second layer and having transparent openings for observing particles, said second layer interposed between and in adherent relationship to said first and third layers, said second layer having a plurality of slots in radial spatial relationship to each other, said slots respectively defining channels for directing liquid conducted by capillary action through chambers respectively defined by said slots in conjunction with said first and third layers and within which chambers agglutination reactions can be performed simultaneously each of said chambers having a proximate zone and a distal zone, said proximate zone comprising a well for receiving a liquid, said liquid flowing to the distal zone of the chamber, each of said slots defining at least approximately parallel walls in the corresponding proximate zone thereby defining a corresponding first path of approximately constant width and defining walls in the corresponding distal zone which are spaced to define a corresponding second path of increased width compared to said first path whereby agglutination reactions in the corresponding chambers result in the formation of a non-random pattern of aggregated particles in said distal zone of said chamber which non-random pattern is visibly observable through said transparent opening of said third layer, and wherein said chamber has a porous absorbent material in liquid communication with said chamber for controlling overall rate of liquid flow through said chamber said porous absorbent material being positioned partially within said second path toward the outer perimeter of said second path in said distal zone along the direction of liquid flow in said first path wherein at least a portion of the porous absorbent material is positioned partially within said distal zone of said chamber, and wherein no portion of said porous absorbent material is in contact with said proximate zone of said chamber and no portion of said porous absorbent material is positioned preceding said proximate zone of said chamber along the direction of liquid flow in said chamber.

18. The device of claim 17 in which said third layer has a well-defining slot and said second layer has a corresponding second well-defining slot of the same size and configuration as said well-defining slot in said third layer and positioned directly below said well-defining slot in said third layer, wherein said second well-defining slot in conjunction with said well-defining slot in said third layer and said first layer define a well for receiving liquid, said well being in liquid communication with said proximate zone of each of said chambers.

19. The device of claim 18 wherein said third layer is hydrophobic.

* * * * *